United States Patent
Yunoki

(10) Patent No.: US 6,949,675 B2
(45) Date of Patent: Sep. 27, 2005

(54) PROCESS FOR PRODUCING ACRYLIC ACID

(75) Inventor: Hiromi Yunoki, Himeji (JP)

(73) Assignee: Nippon Shokubai Co., Ltd., Osaka (JP)

( * ) Notice: Subject to any disclaimer, the term of this patent is extended or adjusted under 35 U.S.C. 154(b) by 102 days.

(21) Appl. No.: 10/228,089

(22) Filed: Aug. 27, 2002

(65) Prior Publication Data

US 2003/0125580 A1 Jul. 3, 2003

(30) Foreign Application Priority Data

Sep. 19, 2001 (JP) .................................. 2001-285033

(51) Int. Cl.$^7$ .............................................. C07C 51/235
(52) U.S. Cl. ...................................... 562/535; 562/532
(58) Field of Search ................................. 562/535, 532

(56) References Cited

U.S. PATENT DOCUMENTS

| | | | |
|---|---|---|---|
| 3,567,772 A | 3/1971 | Yanagita et al. | |
| 3,801,634 A | 4/1974 | Krabetz et al. | |
| 4,223,161 A | 9/1980 | Shaw et al. | |
| 4,415,752 A | 11/1983 | Decker et al. | |
| 5,177,260 A | 1/1993 | Kawajiri et al. | |
| 5,206,431 A | 4/1993 | Hashiba et al. | |
| 5,719,318 A | 2/1998 | Kawajiri et al. | |
| 6,403,829 B1 * | 6/2002 | Unverricht et al. | 562/532 |

FOREIGN PATENT DOCUMENTS

| | | |
|---|---|---|
| DE | WO 00/53559 A1 * | 10/2000 |
| EP | 1 055 662 A1 | 11/2000 |
| GB | 1 488 044 | 10/1977 |
| GB | 1488889 | 10/1977 |
| GB | 1488890 | 10/1977 |
| GB | 1 566 314 | 4/1980 |
| JP | 44-26287 | 11/1969 |
| JP | 50-25914 | 8/1975 |
| JP | 53-30688 | 8/1978 |
| JP | 57-54172 | 11/1982 |
| JP | 3-218334 | 9/1991 |
| JP | 7-10802 | 1/1995 |
| JP | 9-241209 | 9/1997 |
| JP | 2000-336060 | 12/2000 |

* cited by examiner

Primary Examiner—Paul A. Zucker
(74) Attorney, Agent, or Firm—Roylance, Abrams, Berdo & Goodman, L.L.P.

(57) ABSTRACT

The present invention provides a process for producing acrylic acid, by which process the problem, such that the catalyst placed on the gas inlet side deteriorates faster than that placed on the gas outlet side, is solved, so that the catalyst can be used stably for a long time. The process for producing acrylic acid, according to the present invention, comprises the step of carrying out catalytic gas phase oxidation with a fixed-bed shell-and-tube reactor as packed with a catalyst, wherein: used as the catalyst is an oxide shown by the following general formula (1): $Mo_aV_bA_cB_dC_eO_f$ (1) (wherein: A shows at least one member selected from the group consisting of niobium and tungsten; B shows at least one member selected from the group consisting of chromium, manganese, iron, cobalt, nickel, copper, zinc, and bismuth; C shows at least one member selected from the group consisting of phosphorus, tin, antimony, and tellurium); and at least two reaction zones as provided by dividing the inside of each reaction tube in a direction of an axis of the tube in the reactor are packed with the catalyst such that there are regulated the kind and/or amount of the A component and/or the kind and/or amount of the B component.

4 Claims, No Drawings

PROCESS FOR PRODUCING ACRYLIC ACID

BACKGROUND OF THE INVENTION

A. Technical Field

The present invention relates to a process for producing acrylic acid. Specifically, it relates to a process for producing acrylic acid, comprising the step of subjecting acrolein or an acrolein-containing gas to catalytic gas phase oxidation with molecular oxygen or a molecular-oxygen-containing gas using a fixed-bed shell-and-tube reactor as packed with a catalyst.

B. Background Art

As to catalysts which are used in the case of producing acrylic acid by subjecting acrolein or an acrolein-containing gas to catalytic gas phase oxidation, many propositions are made. For examples, JP-B-26287/1969, JP-B-25914/1975, JP-B-54172/1982 and JP-A-218334/1991 are cited. Of these catalysts, some may give acrylic acid with a yield attaining a considerably high level in industrial view, but the below-mentioned problems arise in the case of producing acrylic acid industrially by using these catalysts.

For example, since the industrial production is required to increase the productivity of acrylic acid which is the aimed product, there are generally adopted methods in which the concentration of acrolein which is a raw material is raised or the space velocity is raised. However, the catalytic gas phase oxidation reaction is accompanied by extraordinary heat generation, therefore, under such conditions with a high load, the temperature of a hot spot portion (a locally and extraordinarily high temperature portion in a catalyst layer) goes up by increase of the reacting quantity. As a result, the excess oxidation reaction causes a fall in the yield, or accelerates thermal deterioration of the catalyst, or, in the worst case, may cause a runaway reaction.

Accordingly, to suppress the accumulation of heat in the hot spot portion is very important both for producing acrylic acid in a high yield industrially and for enabling stable operation for a long time by suppressing the deterioration of the catalyst.

As to means to suppress the temperature of the hot spot portion to a low one, several propositions are made. For example, the following methods are proposed: ① a method which involves diluting a catalyst layer, as placed on the gas inlet side, with an inert substance (JP-B-30688/1978); ② a method which involves making the ratio of supporting a catalytically active substance (ratio by weight of the active substance per unit weight of the catalyst) become higher gradually from the gas inlet side toward the gas outlet side (JP-A-10802/1995); ③ a method which involves making the size of the catalyst become smaller gradually from the gas inlet side toward the gas outlet side (JP-A-241209/1997); and ④ a method which involves lowering the activity of a catalyst, as placed on the gas inlet side, by adding an alkaline metal (JP-A-336060/2000).

However, in all the above-mentioned conventional methods ① to ③ to suppress the temperature of the hot spot portion to a low one, since the amount of the catalytically active substance placed on the gas inlet side becomes smaller than that on the gas outlet side, the catalyst placed on the gas inlet side deteriorates faster than that placed on the gas outlet side. As a result, although in view of suppressing the temperature of the hot spot portion to a low one the improvement is achieved in some degree, there arises a problem such that it becomes impossible to continue the reaction for a long time with a high yield kept. Especially, when the reaction is done under conditions with a high load such as using a high concentration of acrolein which is a raw material, this problem becomes striking.

In addition, in the above-mentioned conventional method ④, in view of lowering the activity of the catalyst by "adding" the alkaline metal, the amount of the catalytically active substance placed on the gas inlet side is substantially the same as that on the gas outlet side. However, the addition of the alkaline metal results in decreasing the catalytically active sites, therefore such a catalytic function as corresponds to the amount of the existing catalytically active substance cannot be displayed fully. Accordingly, although the conventional method ④ provides more improved results than the conventional methods ① to ③, the conventional method ④ has not yet succeeded in fully solve the problem such that it becomes impossible to continue the reaction for a long time with a high yield kept.

SUMMARY OF THE INVENTION

A. Object of the Invention

Accordingly, an object of the present invention is to provide a process for producing acrylic acid, by which process the conventional problem, such that the catalyst placed on the gas inlet side deteriorates faster than that placed on the gas outlet side, is solved to make it possible to use the catalyst stably for a long time.

B. Disclosure of the Invention

In order to solve the above-mentioned problems, the present inventor diligently studied. As a result, he has completed the present invention by leading to an idea that if it is made possible to control the activity of the catalyst without essentially changing either the amount of the catalytically active substance in the catalyst placed on the gas inlet side or that on the gas outlet side, then the above-mentioned problems can be solved.

That is to say, a process for producing acrylic acid, according to the present invention, comprises the step of subjecting acrolein or an acrolein-containing gas to catalytic gas phase oxidation with molecular oxygen or a molecular-oxygen-containing gas using a fixed-bed shell-and-tube reactor as packed with a catalyst, and is characterized in that:

used as the catalyst is an oxide and/or a compound oxide having a metal element composition shown by the following general formula (1):

$$Mo_a V_b A_c B_d C_e O_f \qquad (1)$$

(wherein: Mo shows molybdenum; V shows vanadium; A shows at least one element selected from the group consisting of niobium and tungsten; B shows at least one element selected from the group consisting of chromium, manganese, iron, cobalt, nickel, copper, zinc, and bismuth; C shows at least one element selected from the group consisting of phosphorus, tin, antimony, and tellurium; and O shows oxygen; and wherein: when a is 12, then $1 \leq b \leq 14$, $0 < c \leq 12$, $0 < d \leq 10$, $0 \leq e \leq 10$; and f is a numerical value determined by the oxidation state of each element); and at least two reaction zones are provided by dividing the inside of each reaction tube in a direction of an axis of the tube in the fixed-bed shell-and-tube reactor, and the reaction zones are packed with the catalyst in such a manner that the activity of the catalyst is different between the reaction zones by regulating the kind and/or amount of the A component and/or the kind and/or amount of the B component in the general formula (1).

These and other objects and the advantages of the present invention will be more fully apparent from the following detailed disclosure.

DETAILED DESCRIPTION OF THE INVENTION

A catalyst as used in the present invention is an oxide and/or a compound oxide which contains molybdenum and vanadium as essential components and is shown by the above general formula (1). In the general formula (1): Mo shows molybdenum; V shows vanadium; A shows at least one element selected from the group consisting of niobium and tungsten; B shows at least one element selected from the group consisting of chromium, manganese, iron, cobalt, nickel, copper, zinc, and bismuth; C shows at least one element selected from the group consisting of phosphorus, tin, antimony, and tellurium; and O shows oxygen; and wherein: when a is 12, then $1 \leq b \leq 14$, $0 < c \leq 12$, $0 < d \leq 10$, $0 \leq e \leq 10$; and f is a numerical value determined by the oxidation state of each element.

This catalyst can be prepared by methods which are generally used to prepare this type of catalysts. As to starting raw materials which are used for the above catalyst preparation, there is no especial limitation, and useable examples of such include ammonium salt, nitrates, carbonates, sulfates, hydroxides, and oxides of each metal element which are generally used, but a compound containing at least two metal elements may be used.

At least two catalysts displaying different activity, shown by the general formula (1), can be prepared by regulating the kind and/or amount of the A component and/or the kind and/or amount of the B component in the general formula (1). More specifically speaking, the catalysts displaying different activity are obtained by selecting at least one element selected from the group consisting of niobium and tungsten as the A component and/or changing the amount of the selected element within the range of the atomic ratio c prescribed for the general formula (1); or by selecting at least one element selected from the group consisting of chromium, manganese, iron, cobalt, nickel, copper, zinc, and bismuth as the B component and/or changing the amount of the selected element within the range of the atomic ratio d prescribed for the general formula (1).

In addition, the at least two catalysts displaying different activity, shown by the general formula (1), can be prepared not only by the above change of the kind and/or amount of the A component and/or of the B component, but also by a change of the amount of vanadium. More specifically speaking, the catalysts displaying different activity are obtained by changing the amount of vanadium within the range of the atomic ratio b prescribed for the general formula (1).

Incidentally, the "activity" in the present invention means a conversion of a starting raw material.

In the present invention, the catalyst packed in each reaction zone may be a molded catalyst obtained by molding the catalytic component into a certain shape, or a supported type catalyst obtained by supporting the catalytic component on any inert support having a certain shape, or a combination of these molded catalyst and supported type catalyst.

As to the shape of the above catalysts, there is no especial limitation, and it may be any shape of such as spheres, columns (pellets), rings, and irregular shapes. Of course, when the shape of the catalyst is spherical, the shape has no need of being truly spherical and may be substantially spherical. Also as to the shapes of the columns and the rings, the same is applied. In addition, although the shapes of the catalysts packed in the reaction zones may be identical or different (for example; the gas inlet side: a spherical one, the gas outlet side: a pellet-shaped one), usually, the molded catalysts having an identical shape or the supported type catalysts having an identical shape are favorably packed.

As to the size of the above catalyst, when its shape is spherical, the average catalyst particle diameter is favorably in the range of 1 to 10 mm, more favorably in the range of 3 to 8 mm.

When the supported catalyst is used, the material of the support is not especially limited, and there can be used any support which can usually be used to produce a catalyst for producing acrylic acid by gas phase oxidation of acrolein. Specific examples of the useable support include alumina, silica, silica-alumina, titania, magnesia, silica-magnesia, silica-magnesia-alumina, silicon carbide, silicon nitride, and zeolite.

When the supported catalyst is used, the supporting ratio of the catalyst packed in each reaction zone is set suitably so that the most suitable activity and selectivity can be obtained in consideration of such as oxidation reaction conditions and the activity and strength of the catalyst, but it is favorably in the range of 5 to 200%, more favorably in the range of 10 to 100%, particularly favorably in the range of 15 to 50%.

Also as to heat treatment conditions (what is called calcination conditions) when preparing the catalyst, there is no especial limitation, and calcination conditions as adopted generally in production of this type of catalysts can be applied. The heat treatment temperatures of the catalysts packed in the reaction zones may be identical or different, and are favorably in the range of 350 to 450° C., more favorably in the range of 380 to 420° C. The heat treatment time is favorably in the range of 1 to 10 hours.

In the present invention, at least two reaction zones are provided by dividing the inside of each reaction tube in a direction of an axis of the tube in the fixed-bed shell-and-tube reactor, and these at least two reaction zones are packed with the at least two catalysts displaying different activity as prepared by the above-mentioned method.

The method for the above packing arrangement is not especially limited, and examples thereof include: an arrangement of packing such that the activity becomes higher gradually from the gas inlet side toward the gas outlet side; and an arrangement of packing such that the activity once falls and thereafter becomes higher from the gas inlet side toward the gas outlet side. However, favorably, the catalysts displaying different activity are arranged in such a manner that the activity becomes higher gradually from the gas inlet side toward the gas outlet side of each reaction tube, in other words, the catalyst whose activity is the lowest is arranged on the inlet side, and the catalyst whose activity is the highest is arranged on the outlet side. In addition, in the arrangement of packing such that the activity once falls and thereafter becomes higher from the gas inlet side toward the gas outlet side, the packed-layer length of the high active catalyst in the gas inlet part is favorably not longer than 50%, more favorably not longer than 20%, still more favorably not longer than 10%, of total catalyst layers. By arranging the at least two catalysts displaying different activity in the above ways, the accumulation of heat in the hot spot portion can be suppressed, and further, the aimed substance can be obtained with high selectivity stably for a long time.

The number of the reaction zones is not especially limited and, the larger this number is, the easier it becomes to control the temperature of the hot spot portion of the catalyst layer. However, industrially, the aimed effect can be fully obtained by setting the number of the reaction zones at around 2 or 3. In addition, the divisional ratio of the catalyst layer cannot be specified sweepingly, because the best value of the divisional ratio is influenced by such as oxidation reaction conditions and the composition, shape, and size of the catalyst packed in each layer. Therefore the divisional ratio may be selected suitably so that as a whole the best activity and selectivity can be obtained.

When the catalyst is packed into each reaction tube, the catalyst as diluted with an inert substance can also be packed into each reaction zone.

The process for subjecting acrolein or an acrolein-containing gas to catalytic gas phase oxidation with molecular oxygen or a molecular-oxygen-containing gas may be carried out either by the usual one-pass method or the recycling method and, in addition, can be carried out under conditions as used generally for this type of reaction. For example, a mixed gas may be brought into contact with the catalyst at the space velocity of 300 to 5,000 $Hr^{-1}$(STP) in the temperature range of 220 to 450° C. under the pressure of 0.1 to 1 MPa, wherein the mixed gas comprises acrolein 1 to 15 volume %, molecular oxygen of 0.5 to 5 times in volume ratio to this raw gas, and an inert gas as a diluent such as nitrogen, carbon dioxide and water vapor.

If the production process according to the present invention is used, there are advantages as follows: even under conditions with a high load using a high concentration of acrolein, the conventional problem, such that the catalyst placed on the gas inlet side deteriorates faster than that placed on the gas outlet side, is solved, so that the catalyst can be used stably for a long time. That is to say, in the production process according to the present invention, the high concentration of acrolein can be used as a raw material.

As the reaction gas, an acrolein-containing product gas as obtained by subjecting propylene to catalytic gas phase oxidation can be used as it is, without mentioning the mixed gas comprising acrolein, oxygen and the inert gas. In addition, a mixed gas, as obtained by adding air or oxygen and further water vapor into the above-mentioned mixed gas if necessary, can be also used. The acrolein-containing gas, as obtained by oxidizing propylene, contains by-products such as oxidized products (e.g. acrylic acid, acetaldehyde, and acetic acid), carbon oxides, and propane, or propylene, but these are no obstacles to the enforcement of the present invention.

When compared with conventional processes, the process according to the present invention can provide especially much better results under reaction conditions with a high load for the aim to raise the productivity, for example, under conditions of a higher concentration of raw materials or a higher space velocity.

Effects and Advantages of the Invention

In the present invention, the at least two specific molybdenum-vanadium catalysts displaying different activity are packed into catalyst layers respectively which are divided into at least two, thereby giving the following effects:

(a) acrylic acid is obtained in a high yield;

(b) the accumulation of heat in the hot spot portion can be suppressed effectively;

(c) the deterioration of the catalyst by a thermal load can be prevented, so the catalyst can be used stably for a long time; and (d) even if the reaction is done under conditions with a high load such as a high concentration of raw materials or a high space velocity, acrylic acid can be obtained stably in a high yield, so the productivity can greatly be enhanced.

Accordingly, the process according to the present invention is a process that is extremely useful for industrial production of acrylic acid.

DETAILED DESCRIPTION OF THE PREFERRED EMBODIMENTS

Hereinafter, the present invention is more specifically illustrated by the following examples of some preferred embodiments in comparison with comparative examples not according to the invention. However, the invention is not limited to the below-mentioned examples.

The conversion of acrolein, the selectivity of acrylic acid, and the yield of acrylic acid are defined by the following equations:

Conversion of acrolein (mol %)=(molar number of reacted acrolein/molar number of supplied acrolein)×100

Selectivity of acrylic acid (mol %)=(molar number of formed acrylic acid/molar number of reacted acrolein)×100

Yield of acrylic acid (mol %)=(molar number of formed acrylic acid/molar number of supplied acrolein)×100

In addition, the supporting ratio of the catalyst is defined by the following equation:

Supporting ratio (%)=(weight of catalyst after heat treatment–weight of support)/weight of catalyst after heat treatment×100

PRODUCTION EXAMPLE 1

Preparation of Catalyst (1)

While 5,000 ml of water was headed and stirred, thereinto there were dissolved 676 g of ammonium molybdate and 205 g of ammonium metavanadate. Separately, while 200 ml of water was heated and stirred, thereinto there was dissolved 116 g of copper nitrate trihydrate. The resultant two aqueous solutions were mixed together, and further, 23 g of antimony trioxide and 331 g of niobic acid ($Nb_2O_5$ content: 82%) were added thereto, thus obtaining a suspension. This suspension was charged into a porcelain evaporating dish on a hot water bath and then evaporated to dryness while being stirred together with 2,500 g of a silica-alumina support whose average diameter was 5 mm, whereby the catalytic component was allowed to adhere to the support. Then the resultant product was treated by heating under an atmosphere of air at 400° C. for 6 hours, thus obtaining a catalyst (1). The supporting ratio of this catalyst was 30%. The metal element composition excepting oxygen from this catalyst was as follows:

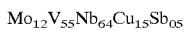

$Mo_{12}V_{55}Nb_{64}Cu_{15}Sb_{05}$

PRODUCTION EXAMPLES 2 AND 3

Preparation of Catalysts (2) and (3)

A catalyst (2) was obtained in the same way as the process for preparing the catalyst (1) of Production Example 1 except that 10 g of potassium nitrate was added. In addition, a catalyst (3) was obtained in the same way as of Production Example 1 except that the amount of niobic acid was changed to 228 g. The metal element compositions excepting oxygen from these catalysts are shown in Table 1.

PRODUCTION EXAMPLE 4

Preparation of Catalyst (4)

While 5,000 ml of water was heated and stirred, thereinto there were dissolved 676 g of ammonium molybdate, 205 g of ammonium metavanadate and 103 g of ammonium paratungstate. Separately, while 200 ml of water was heated and stirred, thereinto there was dissolved 116 g of copper nitrate trihydrate. The resultant two aqueous solutions were mixed together, and further, 23 g of antimony trioxide was added thereto, thus obtaining a suspension. This suspension was evaporated to dryness while its heating and stirring were continued, and then the resultant dry material was dried in the shape of blocks at 120 C. in a drying machine for 5 hours, and then pulverized into the particle diameter of about 100 mesh, thus obtaining a powder. A silica-alumina support of which the average diameter was 5 mm was placed into a centrifugal fluidizing coating apparatus, and then the above powder was placed thereinto together with distilled water as a binder while hot air of 90° C. was passed therethrough, whereby the powder was supported onto the support. Then the resultant product was treated by heating under an atmosphere of air at 400° C. for 6 hours, thus obtaining a catalyst (4). The supporting ratio of this catalyst was 25%. The metal element composition excepting oxygen from this catalyst was as follows:

$$Mo_{12}V_{55}W_{12}Cu_{15}Sb_{0.5}$$

PRODUCTION EXAMPLE 5 and 6

Preparation of Catalysts (5) and (6)

A catalyst (5) was obtained in the same way as the process for preparing the catalyst (4) of Production Example 4 except that the supporting ratio of the catalyst was changed to 20%. In addition, a catalyst (6) was obtained in the same way as of Production Example 4 except that a silica-alumina support of which the average diameter was 8 mm was used. The metal element compositions excepting oxygen from these catalysts are shown in Table 1.

PRODUCTION EXAMPLES 7 to 16

Preparation of Catalysts (7) to (16)

Catalysts (7) to (16) were obtained in the same way as the process for preparing the catalyst (4) of Production Example 4 except that the used amounts of ammonium metavanadate, ammonium paratungstate, niobic acid ($Nb_2O_5$ content: 82%), copper nitrate trihydrate, and ferric nitrate nonahydrate respectively were changed. The metal element compositions excepting oxygen from these catalysts are shown in Table 1.

REFERENTIAL EXAMPLES 1 to 16

The catalysts (1) to (16) as obtained in Production Examples 1 to 16 were packed at a layer length of 1,000 mm into a stainless reaction tube of 25 mm in inner diameter as heated by a molten nitrate, and then a reaction gas having a composition as shown in the below-mentioned reaction gas composition (A) was introduced into the reaction tube at the space velocity of 1,800 $h^{-1}$ (STP) to carry out a catalytic gas phase oxidation reaction of acrolein. The results are shown in Table 2.

Reaction Gas Composition (A):

| Acrolein | 5 volume % |
| Air | 25 volume % |
| Water vapor | 40 volume % |
| Inert gas such as nitrogen | 30 volume % |

Comparative Example 1

A stainless reaction tube of 25 mm in inner diameter, as heated by a molten nitrate, was packed with a catalyst dilution (which was a mixture of alumina balls of 5 mm in average diameter and the catalyst (1) in a volume ratio of alumina balls/catalyst (1)=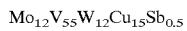) and the catalyst (1) at layer lengths of 600 mm and 2,400 mm respectively in order from the reaction gas inlet side toward the reaction gas outlet side (in other words, the dilution of the catalyst (1) was packed on the reaction gas inlet side, and only the catalyst (1) was packed on the reaction gas outlet side), and then a reaction gas having a composition as shown in the below-mentioned reaction gas composition (B) was introduced into the reaction tube at the space velocity of 2,000 $h^{-1}$ (STP) to carry out a catalytic gas phase oxidation reaction of acrolein for 8,000 hours. The performances of the catalyst in the initial stage of the reaction and after a passage of 8,000 hours are shown in Table 3.

Reaction Gas Composition (B):

| Acrolein | 6 volume % |
| Air | 30 volume % |
| Water vapor | 20 volume % |
| Inert gas such as nitrogen | 44 volume % |

Comparative Examples 2 TO 4, Examples 1 to 8

The reaction was done continuously for 8,000 hours in the same way as of Comparative Example 1 except that the method of packing the catalysts was changed respectively as shown in Table 3. The performances of the catalysts in the initial stage of the reaction and after a passage of 8,000 hours are shown in Table 3.

Comparative Examples 5 and 6, Examples 9 and 10

In Comparative Example 1, the method of packing the catalysts was changed respectively as shown in Table 4, and then a reaction gas having a composition as shown in the below-mentioned reaction gas composition (C) was introduced into the reaction tube at the space velocity of 2,000 $h^{-1}$ (STP) to carry out a catalytic gas phase oxidation reaction of acrolein for 8,000 hours. The performances of the catalyst in the initial stage of the reaction and after a passage of 8,000 hours are shown in Table 4.

Reaction Gas Composition (C):

| Acrolein | 6.5 volume % |
| Air | 35 volume % |
| Water vapor | 20 volume % |
| Inert gas such as nitrogen | 38.5 volume % |

TABLE 1

| Catalyst | Composition of catalyst | | | | | | Particle diameter of catalyst (mm) | Supporting ratio (%) |
|---|---|---|---|---|---|---|---|---|
| | Mo | V | A | B | C | K | | |
| (1) | 12 | 5.5 | Nb6.4 | Cu1.5 | Sb0.5 | 0.3 | 5 | 30 |
| (2) | 12 | 5.5 | Nb6.4 | Cu1.5 | Sb0.5 | | 5 | 30 |
| (3) | 12 | 5.5 | Nb4.4 | Cu1.5 | Sb0.5 | | 5 | 30 |
| (4) | 12 | 5.5 | W1.2 | Cu1.5 | Sb0.5 | | 5 | 25 |
| (5) | 12 | 5.5 | W1.2 | Cu1.5 | Sb0.5 | | 5 | 20 |
| (6) | 12 | 5.5 | W1.2 | Cu1.5 | Sb0.5 | | 8 | 25 |
| (7) | 12 | 5.5 | W0.4 | Cu1.5 | Sb0.5 | | 5 | 25 |
| (8) | 12 | 5.5 | W1.8 Nb1.2 | Cu1.5 | Sb0.5 | | 5 | 25 |
| (9) | 12 | 5.5 | W0.5 Nb0.5 | Cu1.5 | Sb0.5 | | 5 | 25 |
| (10) | 12 | 6.0 | W1.2 | Cu1.5 | Sb0.5 | | 5 | 25 |
| (11) | 12 | 5.5 | W1.2 | Cu4.0 | Sb0.5 | | 5 | 25 |
| (12) | 12 | 5.5 | W1.2 | Cu3.3 Fe0.6 | Sb0.5 | | 5 | 25 |
| (13) | 12 | 5.5 | W1.2 | Cu0.8 Fe0.3 | Sb0.5 | | 5 | 25 |
| (14) | 12 | 6.5 | W1.7 | Cu1.5 | Sb0.5 | | 5 | 25 |
| (15) | 12 | 5.5 | W1.7 | Cu1.2 | Sb0.5 | | 5 | 25 |
| (16) | 12 | 6.8 | W2.1 | Cu1.0 | Sb0.5 | | 5 | 25 |

TABLE 2

| | Catalyst | Reaction temperature (°C.) | Conversion of acrolein (mol %) | Selectivity of acrylic acid (mol %) |
|---|---|---|---|---|
| Referential Example 1 | (1) | 240 | 98.6 | 94.5 |
| Referential Example 2 | (2) | 240 | 87.5 | 95.3 |
| Referential Example 3 | (3) | 240 | 87.8 | 95.7 |
| Referential Example 4 | (4) | 240 | 99.4 | 95.3 |
| Referential Example 5 | (5) | 240 | 90.3 | 96.4 |
| Referential Example 6 | (6) | 240 | 89.3 | 96.2 |
| Referential Example 7 | (7) | 240 | 90.0 | 96.6 |
| Referential Example 8 | (8) | 230 | 99.5 | 95.5 |
| Referential Example 9 | (9) | 240 | 91.3 | 96.4 |
| Referential Example 10 | (10) | 240 | 99.8 | 94.9 |
| Referential Example 11 | (11) | 240 | 90.3 | 96.7 |
| Referential Example 12 | (12) | 240 | 91.0 | 96.6 |
| Referential Example 13 | (13) | 230 | 99.5 | 95.7 |
| Referential Example 14 | (14) | 230 | 99.6 | 95.5 |
| Referential Example 15 | (15) | 230 | 99.2 | 95.9 |
| Referential Example 16 | (16) | 230 | 99.8 | 95.1 |

TABLE 3

| | Method of packing catalysts (gas inlet→gas outlet) | Reaction time (hours) | Reaction temperature (°C.) | Conversion of acrolein (mol %) | Selectivity of acrylic acid (mol %) | Yield of acrylic acid (mol %) |
|---|---|---|---|---|---|---|
| Comparative Example 1 | Catalyst(1) 30% dilution/Catalyst(1) = 600 mm/2400 mm | Initial | 250 | 98.6 | 94.3 | 93.0 |
| | | 8000 | 270 | 98.3 | 94.2 | 92.6 |
| Comparative Example 2 | Catalyst(2)/Catalyst(1) = 600 mm/2400 mm | Initial | 250 | 99.0 | 94.5 | 93.6 |
| | | 8000 | 266 | 98.7 | 94.4 | 93.2 |
| Example 1 | Catalyst(3)/Catalyst(1) = 600 mm/2400 mm | Initial | 250 | 99.1 | 94.8 | 93.9 |
| | | 8000 | 263 | 98.9 | 94.9 | 93.9 |
| Comparative Example 3 | Caralyst(5)/Catalyst(4) = 800 mm/2200 mm | Initial | 245 | 99.2 | 95.1 | 94.3 |
| | | 8000 | 260 | 98.6 | 95.2 | 93.9 |
| Comparative Example 4 | Catalyst(6)/Catalyst(4) = 800 mm/2200 mm | Initial | 245 | 99.0 | 95.0 | 94.1 |
| | | 8000 | 259 | 98.8 | 95.1 | 94.0 |
| Example 2 | Catalyst(7)/Catalyst(4) = 800 mm/2200 mm | Initial | 245 | 99.3 | 95.4 | 94.7 |
| | | 8000 | 255 | 99.2 | 95.4 | 94.6 |
| Example 3 | Catalyst(9)/Catalyst(8) = 800 mm/2200 mm | Initial | 240 | 99.3 | 95.3 | 94.6 |
| | | 8000 | 248 | 99.1 | 95.4 | 94.5 |
| Example 4 | Catalyst(7)/Catalyst(10) = 800 mm/2200 mm | Initial | 240 | 99.3 | 95.4 | 94.7 |
| | | 8000 | 247 | 99.0 | 95.4 | 94.4 |
| Example 5 | Catalyst(11)/Catalyst(4) = 800 mm/2200 mm | Initial | 245 | 99.1 | 95.3 | 94.4 |
| | | 8000 | 255 | 99.0 | 95.3 | 94.3 |
| Example 6 | Catalyst(12)/Catalyst(13) = 800 mm/2200 mm | Initial | 240 | 99.1 | 95.0 | 94.1 |
| | | 8000 | 248 | 99.1 | 94.9 | 94.0 |
| Example 7 | Catalyst(11)/Catalyst(10) = 800 mm/2200 mm | Initial | 245 | 99.3 | 94.9 | 94.2 |
| | | 8000 | 252 | 99.0 | 95.0 | 94.1 |
| Example 8 | Catalyst(11)/Catalyst(10)/Catalyst(14) = 800 mm/1000 mm/1200 mm | Initial | 245 | 99.5 | 94.8 | 94.3 |
| | | 8000 | 251 | 99.4 | 94.6 | 94.0 |

TABLE 4

|  | Method of packing catalysts (gas inlet→gas outlet) | Reaction time (hours) | Reaction temperature (° C.) | Conversion of acrolein (mol %) | Selectivity of acrylic acid (mol %) | Yield of acrylic acid (mol %) |
|---|---|---|---|---|---|---|
| Comparative Example 5 | Catalyst(5)/Catalyst(4) = 800 mm/2200 mm | Initial 8000 | 250 275 | 99.0 98.3 | 94.2 94.2 | 93.3 92.6 |
| Comparative Example 6 | Catalyst(6)/Catalyst(4) = 800 mm/2200 mm | Initial 8000 | 250 275 | 99.1 98.3 | 94.6 94.4 | 93.7 92.8 |
| Example 9 | Catalyst(11)/Catalyst(15) = 800 mm/2200 mm | Initial 8000 | 245 260 | 99.2 99.2 | 94.8 94.7 | 94.0 93.9 |
| Example 10 | Catalyst(11)/Catalyst(15)/Catalyst(16) = 800 mm/1100 mm/1100 mm | Initial 8000 | 245 257 | 99.4 99.1 | 94.8 94.7 | 94.2 93.8 |

Various details of the invention may be changed without departing from its spirit not its scope. Furthermore, the foregoing description of the preferred embodiments according to the present invention is provided for the purpose of illustration only, and not for the purpose of limiting the invention as defined by the appended claims and their equivalents.

What is claimed is:

1. A process for producing acrylic acid, comprising the step of subjecting acrolein or an acrolein-containing gas to catalytic gas phase oxidation with molecular oxygen or a molecular-oxygen-containing gas using a fixed-bed shell-and-tube reactor having a reaction tube packed with a catalyst, with the process being characterized in that:

said catalyst is an oxide and/or a compound oxide having a metal element composition shown by the following general formula (1):

$$Mo_a V_b A_c B_d C_e O_f \qquad (1)$$

(wherein: Mo is molybdenum; V is vanadium; A is at least one element selected from the group consisting of niobium and tungsten; B is at least one element selected from the group consisting of chromium, manganese, iron, cobalt, nickel, copper, zinc, and bismuth; C is at least one element selected from the group consisting of phosphorus, tin, antimony, and tellurium; and O is oxygen; and wherein a is 12, and $1 \leq b \leq 14$, $0 < c \leq 12$, $0 < d \leq 10$, $0 \leq e \leq 10$; and f is a numerical value determined by the oxidation state of each element); and where said reactor has at least two reaction zones by dividing the inside of said reaction tube in a direction of an axis of the tube in the fixed-bed shell-and-tube reactor, and where each of said reaction zones are packed with the catalyst in such a manner that the activity of the catalyst in a first of said reaction zones is different from the activity of a second of said reaction zones by regulating the kind and/or amount of the A component and/or the kind and/or amount of the B component in the general formula (1).

2. A process for producing acrylic acid according to claim 1, further comprising regulating the amount of vanadium in the general formula (1).

3. A process for producing acrylic acid according to claim 1, further comprising packing the catalysts displaying different activity in such a manner that the activity becomes higher gradually from the gas inlet side toward the gas outlet side of each reaction tube.

4. A process for producing acrylic acid according to claim 1, wherein the number of the reaction zones is two or three.

* * * * *